United States Patent [19]

Gairns et al.

[11] Patent Number: 5,278,315
[45] Date of Patent: Jan. 11, 1994

[54] CARBAZOLE COMPOUNDS

[75] Inventors: Raymond S. Gairns, Whitefield; Anthony A. Watson, Cheetham, both of England

[73] Assignee: Imperial Chemical Industries plc, London, England

[21] Appl. No.: 789,027

[22] Filed: Nov. 7, 1991

[30] Foreign Application Priority Data

Nov. 15, 1990 [GB] United Kingdom ............... 9024872

[51] Int. Cl.$^5$ .................. C07D 209/82; C07D 209/88
[52] U.S. Cl. .................................................. 548/440
[58] Field of Search ........................... 548/440, 444

[56] References Cited

PUBLICATIONS

Akao, Chemical Abstracts, vol. 112 (1990) No. 75973j.
Kuroda, Chem. Abstracts, vol. 12 (1990) No. 45667v.
Konishiroku, Chem Abstracts, vol. 103 (1985) No. 113,331x.
Konishiroku, Chem. Abstracts, vol. 103 (1985) No. 113,332y.
Chemical Abstracts—vol. 109, 1988, CA 109(10):83351h, Matsumoto.
Chemical Abstracts—vol. 107, 1987, CA 107(22): 208792v.

*Primary Examiner*—Robert W. Ramsuer
*Attorney, Agent, or Firm*—Cushman, Darby & Cushman

[57] ABSTRACT

A compound of Formula (1):

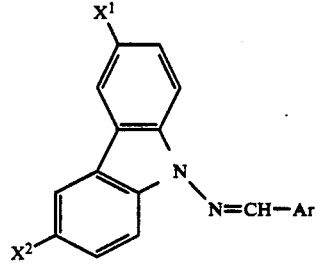

Formula (1)

wherein:
Ar is

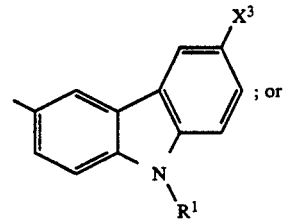

; or

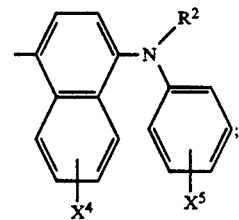

;

$R^1$ is alkyl, substituted alkyl, aryl or substituted aryl, aralkyl or substituted aralkyl;
$R^2$ is alkyl, substituted alkyl, aralkyl or substituted aralkyl;
$X^1$, $X^2$ & $X^3$ are each independently H or a group capable of stabilising a positive charge on the adjacent carbon atom; and
$X^4$ & $X^5$ are each independently H, $C_{1-4}$-alkyl, $C_{1-4}$-alkoxy or $C_{1-4}$-alkylthio;
which is suitable for use as a charge transport compound in organic photoconductors or as a charge control agent in electrophotographic toners.

3 Claims, No Drawings

CARBAZOLE COMPOUNDS

This invention relates to new chemical compounds which are useful as charge transport compounds (CTC) in photoconductor devices and as positive-charging, charge control agents in reprographic toners.

The compounds of the invention, have the general Formula (1):

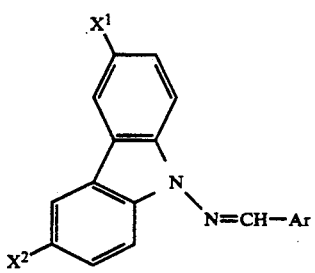

Formula (1)

wherein:
Ar is

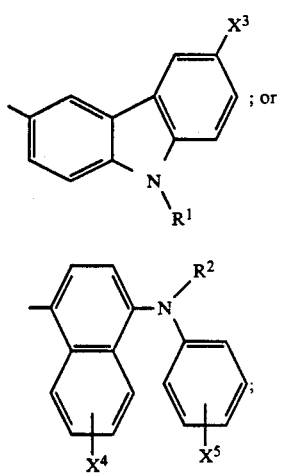

$R^1$ is alkyl, substituted alkyl, aryl or substituted aryl, aralkyl or substituted aralkyl;
$R^2$ is alkyl, substituted alkyl, aralkyl or substituted aralkyl;
$X^1$, $X^2$ & $X^3$ are each independently H or a group capable of stabilising a positive charge on the adjacent carbon atom; and
$X^4$ & $X^5$ are each independently H, $C_{1-4}$-alkyl, $C_{1-4}$-alkoxy or $C_{1-4}$-alkylthio.

When $R^1$ is aryl it preferably has less than seven carbon atoms, and is more preferably optionally substituted phenyl, especially phenyl. When $R^1$ is substituted phenyl the substituent is preferably a group capable of stabilising a positive charge on an adjacent carbon atom, especially $C_{1-4}$-alkyl, $C_{1-4}$-alkoxy or $C_{1-4}$-alkylthio. Examples of such optionally substituted phenyl groups are phenyl, 3-methylphenyl, 4-methylphenyl, 4-methoxyphenyl, 3-aminophenyl and 4-methylthiophenyl.

When $R^1$ or $R^2$ is alkyl, it is preferably optionally substituted $C_{1-4}$-alkyl, especially $C_{1-4}$-alkyl. Examples of such optionally substituted $C_{1-4}$-alkyl groups are methyl, ethyl, propyl, methoxymethyl, methylthiomethyl and dimethylaminomethyl.

When $R^1$ or $R^2$ is substituted the substituent is preferably a group capable of stabilising a positive charge on an adjacent carbon atom. It is, however, preferred that $R^1$ and $R^2$ are both unsubstituted.

When $R^1$ or $R^2$ is optionally substituted aralkyl it preferably has less than 12 carbon atoms and more preferably 7 or 8 carbon atoms, such as naphthyl-$C_{1-2}$-alkyl and phenyl-$C_{1-2}$-alkyl. Examples of optionally substituted aralkyl groups are benzyl, naphthyl-$CH_2$ - and substituted derivatives thereof.

It is preferred that $R^2$ is $C_{1-4}$-alkyl, especially methyl or ethyl, or benzyl.

The group capable of stabilising a positive charge on the adjacent carbon atom is preferably a group which, if it were attached to a benzene ring, would be ortho or para directing towards electrophilic substitution. Such groups include electron donating groups, and groups which are not electron donating but, by virtue of a free electron pair are ortho or para directing. Examples of such groups are $C_{1-4}$-alkyl; $C_{1-4}$-alkoxy; hydroxy; amino; acylamino, especially $C_{1-4}$-alkylcarbonyl; substituted amino, especially tertiary amino such as di-($C_{1-4}$-alkyl) amino; ester, especially $C_{1-4}$-alkylcarboxy; and halo, especially bromo or chloro. The preferred groups are selected from $C_{1-4}$-alkyl, especially methyl; $C_{1-4}$-alkoxy, especially methoxy, and -S-($C_{1-4}$-alkyl), especially -S-$CH_3$. Specific examples of such groups are methyl, methoxy, methylthio, hydroxy, acetamido, amino, dimethylamino and acetoxy. It is preferred that $X^1$, $X^2$ and $X^3$ are all H. It is also preferred that $X^4$ and $X^5$ are both H.

The compounds of Formula (1) are especially useful as charge transport compounds (CTC) in organic photoconductors (OPC) such as are commonly used in electrophotographic copiers and printers. Such OPC generally comprise an electrically conducting substrate carrying a charge generation layer (CGL) and a charge transport layer (CTL) which may be separate or combined in a single phase. Such OPC may be prepared using methods known in the art.

The immediate substrate is an electrically conducting material, which may be provided (a) by a rigid metal, e.g. aluminum, support, preferably in the form of a drum; or (b) by a composite material, in the form of a drum or a continuous belt, comprising an insulating support such as a sheet or film of polymeric material, e.g. a polyester, coated with a thin film of an electrically conducting material, e.g. aluminum.

The CGL may comprise charge generating compound (CGC) alone preferably in the form of a layer deposited on the substrate, or the CGC may be dispersed in a resin and formed into a layer on the substrate. Examples of suitable resins for use in the CGL are polycarbonate, polyester, polystyrene, polyurethane, epoxy, acrylic, styrene-acrylic, melamine, polyvinylbutyral and silicone resins. Where the resin (e.g. a polycarbonate) does not have good adhesive properties with respect to the substrate, adhesion between the resin and the substrate may be improved by the use of an adhesive resin. A specific example of a suitable resin for use in the CGL is LEXAN 141 Natural (General Electric Plastics, Europe). A suitable adhesive resin for bonding the CGL to the substrate is VMCA (Union Carbide).

Suitable CGC for use in the CGL include dyes and especially pigments of various chemical types, for example azo, squaraine, thiapyrilium, phthalocyanine and polycyclic aromatic carbonyl compounds. Preferred CGC are X-form metal free phthalocyanine and titanyl phthalocyanine in the alpha, gamma or T forms.

The CTL preferably comprises a layer of a resin containing the CGC of Formula (1) and preferably has a thickness from 1.0 micrometer to 50 micrometers and more preferably from 5.0 micrometers to 30 micrometers. Examples of suitable resins for use in the CTL include one or more of polycarbonate, polyester, polystyrene, polyurethane, epoxy, acrylic, styrene-acrylic, melamine and silicone resins. A preferred resin for use in CTL is LEXAN 141.

The new compounds of the present invention are also suitable as colorless charge control agents (CCA) for use in electrophotographic toners, especially positive charging toners. The CCA are especially valuable in two component systems (toner+carrier) but are also suitable for one-component toners and liquid toners.

The invention is illustrated by the following Examples in which all parts and percentages are by weight unless otherwise stated. Examples 1 to 5 describe the preparation of compounds of Formula (2).

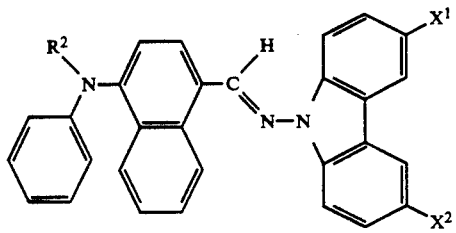

EXAMPLE 1

Preparation of the compound of Formula (2) in which $R^2$ is methyl and $X^1$ and $X^2$ are both H

Stage 1—N-Aminocarbazole

To a stirred mixture of carbazole (MW 163, 0.1M, 16.3 g) and KOH (85%, 1.35M, 89.1 g) in dimethylformamide (DMF, 180 ml) at 0°–10 °C. was added hydroxylamine-o-sulphonic acid (MW 113, 0.2M, 22.6 g) over 15 minutes, maintaining the temperature at <10° C. The mixture was allowed to warm to room temperature and stirred for 3 hours. The suspension was poured into water (700 ml) and after stirring for 10 minutes, filtered off, and washed alkali-free with cold water. The resultant paste was redissolved in dichloromethane (130 ml), screened to remove insoluble matter, dried over $MgSO_4$ and solvent removed under reduced pressure to give a crude grey solid (8 g) which was estimated to contain approximately 4 g of N-amino-carbazole.

Stage 2—1-(N-Methyl-N-phenylamino)-naphthalene

A mixture of 1-(N-phenylamino)-naphthalene (MW 219, 0.05M, 11 g), iodomethane (MW 142, 0.1M, 14.2 g), copper bronze (1 g), and KOH (85%, 0.1M, 6.6 g) in N-methyl pyrrolidone (NMP, 20 ml) was stirred at 120 °C. under nitrogen for 3 hours. After cooling to 30° C., water (150 ml) was added. The mixture was extracted using dichloromethane (2×75 ml) and the extracts washed with water, dried over $MgSO_4$ and screened through silica gel (MERCK 60H Art 7736) to give a solution. The solvent was evaporated from the solution under reduced pressure to give 8.9 g of an oil (76% yield).

An infra red absorption ("IR") spectrum showed absorbance peaks at 3060, 1600, 1570, 1500, 1390, 1330, 1270, 1110, 1030, 775, 750 and 690 $cm^{-1}$. $^1H$ nmr (250 $MH_z$ in $CDCl_3$) showed peaks at 3.3 (3H, S), 6.4–7.9 (12H, m).

Stage 3—1-(N-Methyl-N-phenylamino)-4-formyl-naphthalene

Phosphorus oxychloride ($POCl_3$, MW 153, 0.06M, 9.18 g) was added dropwise to DMF (MW 73, 0.36M, 26.3 g), maintaining the temperature at <10° C. with external cooling. 1-(N-Methyl-N-phenylamino)-naphthalene (MW 233, 0.06M, 14 g) was added and the reaction stirred at 100° C. for 3 hours. After cooling to room temperature and pouring into water (140 ml) the mixture was neutralised to pH 6 using saturated sodium acetate solution. The aqueous mixture was extracted using dichloromethane (2×50 ml), the combined extracts washed with water (3×100 ml) before drying over $MgSO_4$. The solvent was evaporated under reduced pressure to give 10.4 g of 1-(N-methyl-N-phenylamino)-4-formyl naphthalene as an oil (66% yield).

An IR spectrum of the product showed absorbance peaks at 3060, 2820, 2740, 1680, 1600, 1510, 1470, 1430, 1390, 1355, 1310, 1230, 1165, 1140, 1120, 1010, 820, 810, 780 and 690 $cm^{-1}$.

$^1H$ nmr (250 $MH_z$ in $CDCl_3$) showed peaks at 3.5 (3H, S), 6.55–7.97 (11H, m) and 9.74 (1H, S).

The mass spectrum showed peaks at 261 ($M^+$, 100%), 233 and 217.

Stage 4—Title Compound

A mixture of 1-(N-methyl-N-phenylamino)-4-formyl-naphthalene (MW 261, 0.1M, 26.1 g), N-aminocarbazole (MW 182, 40%, 46 g), HCl, S.G.1.18 (9 ml) and ethanol 74 OP (1 liter) was stirred at room temperature for 3 hours. After neutralising to pH 7 (2N NaOH), the precipitate was filtered off and washed with ethanol before being purified by flash chromatography on silica gel (MERCK 60H Art 7736) using dichloromethane/petrol 40–60 as eluant. Solvent was removed in vacuo from the combined chromatography fractions to give 17.45 g of title product (42% yield) as a yellow solid, m.p.141°–142 ° C.

An IR spectra of the title product showed absorbance peaks at 3060, 1610, 1590, 1515, 1480, 1442, 1390, 1330, 1310, 1220, 1180, 1140, 1110, 1010, 820, 775, 745 and 715 $cm^{-1}$.

$^1H$ nmr (250 $MH_z$ in $CDCl_3$) showed peaks at 3.49 (3H, S), 6.63–8.1 (19H, m) and 8.9 (1H, S).

The mass spectrum showed peaks at 425 ($M^+$, 100%), 259, 232, 217 and 166.

EXAMPLE 2

Preparation of the compound of Formula (2) in which $R^2$ is ethyl and $X^1$ and $X^2$ are both H

Stage 1—1-(N-Ethyl-N-phenylamino)-naphthalene

This was prepared using the process described in Stage 2 of Example 1, except that iodoethane (MW 156, 0.15M, 23.4 g) was used in place of iodomethane and the amount of KOH was increased to 0.15M, (9.9 g) to give (N-ethyl-N-phenylamino)-naphthalene (8 g) as an oil (65% yield).

An IR spectra of the product showed absorbance peaks at 2980, 1600, 1500, 1395, 1270, 1120, 800, 775, 750 and 690 $cm^{-1}$.

$^1$H nmr (250 MH$_z$ in CDCl$_3$) showed peaks at 1.32 (3H, t, J=8Hz), 3.9 (2H, q, J=8Hz) and 6.5-7.96 (11 H, m).

The mass spectrum showed peaks at 247 (M+), 232 (100%), 217, 127 and 104.

Stage 2—1-(N-Ethyl-N-phenylamino)-4-formyl-naphthalene

This was prepared using the process described in Stage 3 of Example 1, except that in place of 1-(N-methyl-N-phenylamino)naphthalene there was used 1-(N-ethyl-N-phenylamino)-naphthalene (MW 247, 0.05M, 12.4 g), the amount of POCl$_3$ was reduced to 7.65 g and the amount of dimethyl formamide was reduced to 21.9 g. (N-Ethyl-N-phenylamino)4-formyl-naphthalene (11 g) was obtained as a yellow oil (80% yield).

An IR spectra of the product showed absorbance peaks at 2980, 1670, 1590, 1510, 1395, 1340, 1310, 1270, 1230, 1165, 1140, 855 and 775 cm$^{-1}$. $^1$H nmr (250 MH$_z$ in CDCl$_3$) showed peaks at 1.32 (3H, t, J=8Hz), 3.9 (2H, q, J=8Hz), 6.5-7.96 (11H, m) and 9.73 (1H, S).

The mass spectrum showed peaks at 275 (M+), 260 (100%), 230, 217 and 232.

An IR spectra of the product showed absorbance peaks at 2980, 1670, 1590, 1510, 1395, 1340, 1310, 1270, 1230, 1165, 1140, 855 and 775 cm$^{-1}$. $^1$H nmr (250 MH$_z$ in CDCl$_3$) showed peaks at 1.32 (3H, t, J=8Hz), 3.9 (2H, q, J=8Hz), 6.5-7.96 (11H, m) and 9.73 (1H, S).

The mass spectrum showed peaks at 275 (M+), 260 (100%), 230, 217 and 232.

Stage 3—Title Compound

The title compound was prepared using the process described in Stage 4 of Example 1, except that in place of 1-(N-methyl-N-phenylamino) -4-formyl-naphthalene there was used 1-(N-ethyl-N-phenylamino)-4-formyl-naphthalene (MW 275, 0.0049M, 1.35 g), the amount of N-aminocarbazole was reduced to 2.23 g, the amount of HCl was reduced to 0.44 ml and the amount of ethanol was reduced to 50 ml. The title compound (0.6 g) was obtained as a yellow solid, m.p. 82°-84° C.

An IR spectra of the title compound showed absorbance peaks at 3040, 1610, 1590, 1510, 1445, 1395, 1330, 1310, 1270, 1230, 1180, 820, 800, 775, 750 and 720 cm$^{-1}$. p $^1$H nmr (250 MH$_z$ in CDCl$_3$) showed peaks at 1.34 (3H, t, J=8Hz), 3.91 (2H, q, J=8Hz), 6.57-8.11 (19H, m) and 8.88 (1H, S).

The mass spectrum showed peaks at 439 (M+, 100%), 257, 244, 231, 217 and 167.

EXAMPLE 3

Preparation of the compound of Formula (2) in which R$^2$ is benzyl and X$^1$ and X$^2$ are both H Stage 1—1-)N-Benzyl-N-phenylamino)-naphthalene Benzyl bromide (MW 171, 0.15M, 25,6 g) was added dropwise to a stirred mixture of 1-(N-phenylamino)-naphthalene (MW 219, 0.1M, 21.9 g), KOH (85%, MW 56, 0.15M, 9.9 g) and NMP (70 ml) at 120° C. The mixture was stirred for a further 2 hours at 120° C. and then poured into water, the solid filtered and wash). The solid product was crystallised from methanol to give a white solid (20 g, 65% yield).

An IR spectrum of the product showed absorption peaks at 2960, 1730, 1590, 1570, 1490, 1450, 1390, 1350, 1290, 1265, 1120, 1070, 745 and 690 cm$^{31\ 1}$. $^1$H nmr (250 MHz in CDCl$_3$) showed peaks at 5.0 (2H,S), 6.54-7.92 (17H,m).

The mass spectrum showed peaks at 309 (M+, 100%), 218, 180 and 91.

Elemental analysis gave C: 88.7 H: 6.3% N: 4.2.

Calculated C: 89.3 H: 6.1% N:4.5.

Stage 2—1-(N-Benzyl-N-phenylamino)-4-formyl-naphthalene

This was prepared by the process of Example 1, Stage 3 except that the 1-(N-methyl-N-phenylamino)-naphthalene was replaced by 1-(N-benzyl-N-phenylamino)-naphthalene (MW 309, 0.063M, 19.5 g), the amount of POCl$_3$ was increased to 9.6 g and the amount of DMF was increased to 27.6 g to give the title product as a yellow oil (11.9 g, 56% yield).

An IR spectrum of the product showed absorption peaks at 3060, 1670, 1595, 1560, 1510, 1395, 1350, 1310, 1165, 985, 820, 775, 730 and 700 cm$^{-1}$.

$^1$H nmr (250 MHz in CDCl$_3$) showed peaks at 5.04 (2H,S), 6.55-8.0 (16H,m) and 9.7 (1H,S).

The mass spectrum showed peaks at 337 (M+, 100%) 218 and 91.

Elemental analysis gave C: 82.8 H: 5.8 N: 3.9.

Calculated C: 85.5 H: 5.6 N: 4.1.

Stage 3-N-(1-[N-Benzyl-N-phenylamino]-naphth-4-yl-carbazole)

This was prepared by the process of Example 1, Stage 4, except that the 1-(N-methyl-N-phenylamino)-4-formyl-naphthalene was replaced by the product from Stage 2 above (MW 337, 0.0049M, 1.65 g), the amount of N-aminocarbazole was reduced to 1.78 g (0.0049M), the amount of HCl (SG 1.18) was reduced to 0.4ml and the amount of ethanol (74 OP) was reduced to 50 ml, to give the title product as a yellow solid (1.2 g, 49% yield) m.p. 110°-4° C.

An IR spectrum of the product showed absorption peaks at 3060, 1610, 1590, 1510, 1480, 1440, 1390, 1350, 1330, 1310, 1290, 1230, 1180, 1120, 780, 750 and 720 cm$^{-1}$.

$^1$H nmr (250 MHz in CDCl$_3$) showed peaks at 5.04 (2H,S), 6.6-8.1 (24H,m) and 8.84 (1H,S).

The mass spectrum showed peaks at 501 (M+), 244, 217, 166 and 28 (100%).

EXAMPLE 4

Preparation of the compound of Formula (2) in which R$^2$ is methyl, X$^1$ is H and X$^2$ is bromine Stage 1—3-Bromocarbazole Bromine (MW 160, 0.05M, 8 g) was added dropwise to a stirred mixture of carbazole (MW 167, 0.05M, 8.35 g) in acetic acid (50 ml). After stirring for a further 15 minutes, the reaction mixture was poured into cold water and the precipitated product filtered, washed and recrystallised from methanol to give a solid product, m.p. 191° C. An IR spectrum gave absorption peaks at 3400, 1690, 1470, 1445, 1430, 1330, 1285, 1270, 1235, 1050, 920, 875, 810, 745 and 725 cm$^{-1}$.

The mass spectrum showed peaks at 245 (M+H+, 100%), 166, 139, 123 and 83.

Elemental analysis gave C: 57.1 H: 3.3 N: 7.1 Br: 29.6.

Calculated C: 58.9 H: 3.3 N: 5.7 Br: 32.7.

Stage 2—N-Amino-3-bromocarbazole

This was prepared by the process of Example 1, Stage 1, except that the carbazole was replaced by 3-bromocarbazole (MW 245, 0.5M, 12.3 g), the amount of KOH was reduced to 23.1 g, the amount of DMF was reduced to 100 mls and the amount of hydroxylamine-o-sulphonic acid was reduced to 11.3 g, to give 4.7 g of a grey solid.

Stage 3—Title Compound

This was prepared by the process of Example 1, Stage 4 except that the amount of 1-(N-methyl-N-phenylamino)-4-formyl-naphthalene was reduced to 2.35 g (0.009M), N-amino-3-bromocarbazole (MW 261 50% paste, 0.009M, 4.7 g) was used in place of N-aminocarbazole, the amount of HCl (SC 1.18) was reduced to 1 ml and the amount of ethanol (74 OP) was reduced to 30ml, to give a yellow solid (0.3 g, 7% yield), m.p. 100°-3° C.

An IR spectrum showed absorption peaks at 1610, 1590, 1570, 1510, 1470, 1440, 1390, 1350, 1300, 1270, 1230, 1180, 1100, 1010, 820, 800, 770 and 730 cm$^{-1}$.

$^1$H nmr (250MHz in CDCl$_3$) showed peaks at 3.49 (3H,S), 6.57-8.47 (18H,m) and 9.12 (1H,S).

The mass spectrum showed peaks at 505 (M+H$^+$), 245 (100%), 166 and 139.

Elemental analysis gave C: 71.3 H: 4.6 N: 7.9 Br: 16.2.
Calculated C: 71.4 H: 4.4 N: 8.3 Br: 15.9.

EXAMPLE 5

Preparation of the compound of Formula (2) in which R$^2$ is methyl and X$^1$ and X$^2$ are both bromine

Stage 1—3,6-Dibromocarbazole

This was prepared by the process of Example 4 Stage 1 except that the amount of bromine was increased to 32 g (0.2M), the amount of carbazole was increased to 16.7 g (0.1M) and the amount of acetic acid was increased to 100ml to give a grey solid (24.3 g, 75% yield).

An IR spectrum showed peaks at 3400, 1470, 1455, 1450, 1430, 1330, 1285, 1135, 1050, 870, 810, 750 and 725 cm$^{-1}$.

The mass spectrum showed peaks at 325 (M$^-$), 245, 209, 167.

Stage 2—N-Amino-3,6-dibromocarbazole

This was prepared by the process of Example 4, Stage 2 except that the 3-bromocarbazole was replaced by 3,6-dibromocarbazole (MW 325, 0.05M, 16.3 g), to give a grey solid (14 g).

Stage 3—Title Compound

This was prepared by the process of Example 1, Stage 4 except that N-amino-3,6-dibromocarbazole (MW 340, 50% paste, 0.01M, 6.8 g) was used in place of N-aminocarbazole, the amount of HCl (SG 1.18) was reduced to 0.9ml, the amount of 1-(N-methyl-N-phenylamino)-4-formylnaphthalene was reduced to 2.61g (0.01M) and the amount of ethanol (174 OP) was reduced to 100ml, to give a yellow solid (0.37 g, yield 6%), m.p. 172°-6° C.

An IR spectrum showed absorption peaks at 1710, 1610, 1590, 1570, 1510, 1465, 1430, 1390, 1350, 1310, 130, 1280, 1175, 1140, 1100, 1029, 800 and 770 cm$^{-1}$.

$^1$H nmr (250 MHz in CDCl$_3$) showed peaks at 3.48 (3H,S), 6.57-8.55 (17H,m) and 9.06 (1H,S).

The mass spectrum showed peaks at 583 (M$^+$, 100%), 259, 232 and 217.

Elemental analysis gave C: 63.7 H: 3.8 N: 7.1 Br: 25.2.
Calculated C: 61.7 H: 3.6 N: 7.2 Br: 27.4.

EXAMPLE 6

Preparation of the compound of Formula (3)

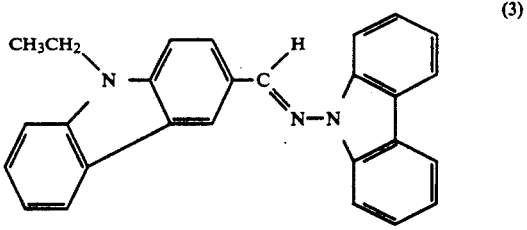

A mixture of N-aminocarbazole (MW 182, 50% strength, 0.01M, 3.64 g) and N-ethyl-3-formyl-carbazole (MW 223, 0.01M, 2.23 g) in HCl (SG 1.18, 0.01M, 0.88ml) and ethanol 74 OP (50ml) was stirred at room temperature for 1 hour, then basified to pH 7 (2N NaOH) and the precipitate filtered off and washed with ethanol 74 OP (100ml). The solid product was redissolved in dichloromethane (50ml), the solution screened through silica gel (MERCK 60H Art 7736) and the dicholoromethane evaporated under reduced pressure to give a yellow-white solid (2.55 g, 66% yield) m.p. 148°-149° C.

An IR spectra showed absorbance peaks at 3060, 2980, 1625, 1600, 1490, 1475, 1445, 1380, 1330, 1310, 1290, 1235, 1150, 800, 750 and 720 cm$^{-1}$.

$^1$H nmr (250 MH$_z$ in CDCl$_3$) showed peaks at 1.5 (3H, t, J=8Hz), 4.4 (2H, q, J=8Hz), 7.18-8.63 (15H, m) and 9.22 (1H, S).

The mass spectrum showed peaks at 387 (M$^+$, 100%), 205, 194, 179 and 167.

EXAMPLES 7-12 AND COMPARATIVE EXAMPLE 1 (CE1)

Metal-free phthalocyanine (0.45 g) and polyester resin (VITEL PE200 from Goodyear) (0.45 g) were added to a bottle containing 3mm glass beads (25 g) and 4:1 dichloromethane:toluene (DCM/T) (10ml) and shaken for 1h on a Red Devil paint shaker. The dispersion was diluted with 4:1 DCM/T (10ml), coated onto 100 micron aluminised polyester film (MELINEX from ICI), using a 6 micron (wet thickness) wire-wound bar and dried to form a charge generation layer (CGL). The polyester film had been precoated with a 2% wt/v solution of an adhesive polymer in 4:1 DCM/T using a 6 micron (wet thickness) wire-wound bar. The CGL was overcoated with an 8.6% wt/wt solution of a charge transport compound (CTC) as identified in Table 1 in a 9.4% wt/v solution of polyester resin (VITEL PE200) in MEK using a 150 micron (wet thickness) wire-wound bar, dried at 70° C. for 3 hours to form an OPC comprising a CGL and a CTL.

Each OPC was tested using a Kawaguchi Electric Works Model SP428 Electrostatic Paper Analyser, in the dynamic mode. The following properties were measured:

V$_1$ Surface potential (volt) of sample after 10 seconds charging with a 6 kV corona.

V$_2$ Surface potential (volt) after 5 seconds in dark conditions.

DD Dark decay (%) given by the expression:

$$DD = \frac{V_1 - V_2}{V_1} \times 100$$

S Sensitivity (lux sec): the product of the light intensity (hue) and the time (sec) taken to reduce the surface potential by 50%.

$V_r$ Residual Potential (volt) remaining on surface after illumination for 10 sec.

The results are in Table 1:

TABLE 1

| Example | CTC | $V_1$ (volts) | $V_2$ (volts) | DD (%) | S (lux sec) | $V_r$ (volt) |
|---|---|---|---|---|---|---|
| 7 | Ex 1 | 1050 | 740 | 30 | 0.8 | 5 |
| 8 | Ex 2 | 1100 | 870 | 21 | 1.1 | 20 |
| 9 | Ex 3 | 1100 | 870 | 21 | 1.4 | 30 |
| CE1 | "A" | 1050 | 810 | 23 | 1.3 | 60 |
| 10 | Ex 4 | 630 | 440 | 30 | 0.8 | 50 |
| 11 | Ex 5 | 650 | 480 | 26 | 0.7 | 40 |
| 12 | Ex 6 | 740 | 590 | 20 | 0.8 | 30 |

CTC "A" is the compound of Formula (2) in which $R^2$ is phenyl and $X^1$ and $X^2$ are both H.

We claim:

1. A compound of formula (1):

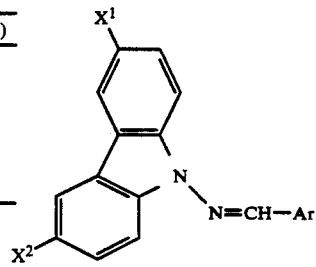

Formula (1)

wherein:

Ar is

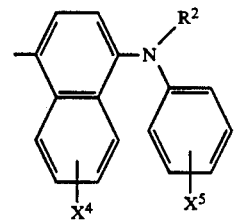

$R^2$ is alkyl, substituted alkyl, aralkyl or substituted aralkyl;

$X^1$ and $X^2$ are each independently H or a group capable of stabilizing a positive charge on the adjacent carbon atom; and $X^4$ and $X^5$ are each independently H, $C_{1-4}$-alkyl, $C_{1-4}$-alkoxy or $C_{1-4}$alkylthio.

2. A compound according to claim 1 wherein $R^2$ is phenyl-$C_{1-4}$-alkyl or $C_{1-4}$-alkyl.

3. A compound according to claim 1 wherein $R^2$ is ethyl.

* * * * *